(12) United States Patent
Kim

(10) Patent No.: US 8,535,057 B2
(45) Date of Patent: Sep. 17, 2013

(54) DENTAL FILING TOOL

(76) Inventor: Daniel Sung-Yul Kim, Vancouver, WA (US)

( * ) Notice: Subject to any disclaimer, the term of this patent is extended or adjusted under 35 U.S.C. 154(b) by 1749 days.

(21) Appl. No.: 11/271,291

(22) Filed: Nov. 12, 2005

(65) Prior Publication Data

US 2006/0093991 A1    May 4, 2006

Related U.S. Application Data

(63) Continuation-in-part of application No. 10/945,033, filed on Sep. 21, 2004, now abandoned.

(51) Int. Cl.
*A61C 3/06* (2006.01)
(52) U.S. Cl.
USPC .......................................................... 433/142
(58) Field of Classification Search
USPC .................. 433/142, 148, 149; 132/321, 329
See application file for complete search history.

(56) References Cited

U.S. PATENT DOCUMENTS

| | | | | |
|---|---|---|---|---|
| 788,947 A | * | 5/1905 | Roth | 132/323 |
| 1,201,875 A | * | 10/1916 | Russ | 433/142 |
| 2,702,555 A | * | 2/1955 | De Mar | 264/249 |
| 2,730,804 A | * | 1/1956 | Saupe | 433/142 |
| 2,736,327 A | * | 2/1956 | Schlicksupp | 132/323 |
| 2,771,085 A | * | 11/1956 | Fleming | 132/321 |
| 3,624,908 A | * | 12/1971 | Ricketts et al. | 433/118 |
| 4,030,198 A | * | 6/1977 | Gerber | 433/142 |
| 4,592,729 A | * | 6/1986 | Bilciurescu | 433/142 |
| 5,084,978 A | * | 2/1992 | McReynolds | 30/517 |
| 6,386,873 B1 | * | 5/2002 | Blank | 433/142 |
| 6,508,649 B2 | * | 1/2003 | Gratz | 433/142 |

FOREIGN PATENT DOCUMENTS

JP    7-194618    * 6/1993

* cited by examiner

*Primary Examiner* — Ralph Lewis
(74) *Attorney, Agent, or Firm* — Kurt M. Rylander; Mark E. Beatty; Rylander & Associates P.C.

(57) ABSTRACT

A disposable dental filing tool having a handle easy to hold between fingers which arches over and secures at both ends of a thin filing strip. The filing strip can be coated with superfine abrasive material. The filing strip can also be a sharp cutting system along the edge or lateral surface. The strip is fastened between each end of the handle with sufficient tension in the strip to create a rigid filing and grinding surface. The handle is made from formable materials into which a filing strip is inserted. On the outside edge of each vertical arm of the handle is a smooth flattened surface to place fingers to hold the handle.

6 Claims, 3 Drawing Sheets

DENTAL FILING TOOL

This application is a continuation in part of and claims priority to nonprovisional patent application Ser. No. 10/945,033 filed Sept. 21, 2004 now abandoned.

BACKGROUND OF THE INVENTION

This invention relates to dental filing tool, more particularly to a dental filing tool that holds a thin filing strip coated with superfine abrasive material or has a sharp cutting edge for efficient filing of the interproximal area and fitting of dental crowns, bridges, onlays, inlays and fillings.

The current conventional method for fitting dental crowns, bridges, onlays and inlays, herein referred to generally as restorations, involves the dental practitioner sliding colored carbon paper, the thickness of which is the recommended measured distance between teeth, in between the interproximal area of the tooth and the restoration. The carbon paper marks with carbon ink the proximal contact area where the two surfaces of the teeth and/or restoration are too close, and then the practitioner grinds the restoration with a rotary instrument to remove excess material. This method is tedious, inefficient, and inexact. The dental practitioner has to continually remove the restoration and grind the heavy proximal contact surface until the fitting surface and shape is achieved. The practitioner first must insert the carbon marker to gauge the distance between the restoration and tooth, withdraw the carbon marker, remove the restoration, and then grind the surface of the restoration marked by the carbon ink with a separate rotary instrument or a freestanding grinding machine which often is in another area away from the patient. Then return to the patient to fit the restoration, and then start the process all over again until the desired distance between the restoration and the adjacent teeth is achieved. It is a time consuming process and there is possibility of over-grinding, in which case a whole other replacement restoration must be reconstructed which involves an expensive lab fee for the practitioner and wasted time for the patient and the practitioner, not to mention it is inconvenient for the patient who suffers for the delay and pain.

Another method employed is the stand-alone use of a metal filing strip coated with some superfine abrasive material. The metal filing strip is inserted between the interproximal area to file down the proximal contact area of the crown for an accurate fit. Since the space between the tooth and the crown, bridge, onlay, and inlay must not be too close nor too spaced apart the practitioner must file increments at a time. These steps are repeated until the desired distance between the tooth and the restoration is achieved. Because the filing strip is extremely thin, narrow, and malleable, it is necessary for the practitioner to create rigid tension in the strip by holding it taunt at opposite ends with fingers from both hands. Unfortunately holding the filing strip in such as manner is cumbersome in the patient's mouth and impedes the practitioner from achieving desired angles and restricts range of motion to effectively file. Especially when the patient is receiving crowns, bridges, onlays, or inlays in the back of the mouth where it is considerably more difficult to access, it is difficult for the practitioner to file since both hands are needed to hold tension in the strip and often a patient's mouth is too small and cannot open wide enough to accommodate comfortably. As a result, the patient must endure strenuous stretching of the lips and jaw area. Often a practitioner struggles to find the best placement for fingers to pinch the strip to create sufficient tension while attempting to minimize the imposing presence of both hands in the patient's mouth. This method is inefficient, tiresome for the practitioner, and uncomfortable for the patient. Moreover, because of the difficulty involved handling the filing strip, often patients sustain suffer small cuts due to the sharp edges of the strip coming in contact with gums and lips while filing the tooth or restoration.

Another method employed is that of a thin metal strip coated with fine abrasive material is fastened to a removable bow which is attached a handle. This bow and handle are too long to maneuver in the mouth and limit the optimal length of the abrasive strip. The strip itself is the important working surface in interproximal filing and the short length of the strip in this method is ineffective because the strip itself is too short to effectuate a sawing motion to file away material, particularly for posterior teeth. Also in this method, it is a hassle to replace the filing strip after each use.

In order to solve the existing problems with the current methods for interproximal grinding and adjustment between restorations and teeth, it is the object of the present invention to provide a tool that has a body that secures a filing strip with sufficient tension that can be held by one hand between opposable fingers. This allows for the practitioner to maneuver within the patient's mouth with easier reach and greater range of motion for more time efficient and effective filing and grinding of the interproximal area with greater comfort for the patient for a quicker fitting of crowns, bridges, onlays, and inlays.

SUMMARY OF THE INVENTION

The main object of the present invention is to provide a filing tool which secures a filing strip with sufficient tension, that is easy to hold and maneuver while inserted in a patient's mouth to efficiently and effectively file and grind between teeth and the crown, bridge, onlay, or inlay for an accurate fitting.

Another object of the present invention is to provide a filing tool that inflicts the least amount of discomfort and injury to patient's gums and lips during filing.

Accordingly, the present invention is comprised of a handle made of a formable material, not limited to but like plastic, which has a horizontal arm element with a first vertical arm extending downward from its first end and a second vertical arm extending from its second end forming an arch. Between the first and second vertical arms a filing strip is secured at each end tautly with tension. The horizontal arm which arches above and flush with the filing strip from its top edge tapers downwards towards the filing strip reducing in thickness to a fine beveled edge. The horizontal arm which arches above and flush with the filing strip has a middle portion with a reinforcing raised flat segment on both sides of the horizontal arm that increases thickness to achieve rigidity. Additionally, the first and second vertical arms of the handle also taper in thickness from the outside edge inwards towards the filing strip reducing in thickness to a fine beveled edge. The outside wider edges of the first and second vertical arms have a flattened surface area on which opposable fingers may be placed to hold the invention to facilitate an easy sawing back and forth movement to file.

The above and other objects, features, and advantages of the present invention will be fully understood from the following description considered in connection with the accompanying drawings included.

BRIEF DESCRIPTIONS OF THE DRAWINGS

DETAILED DESCRIPTION OF THE INVENTION

Figure 1:
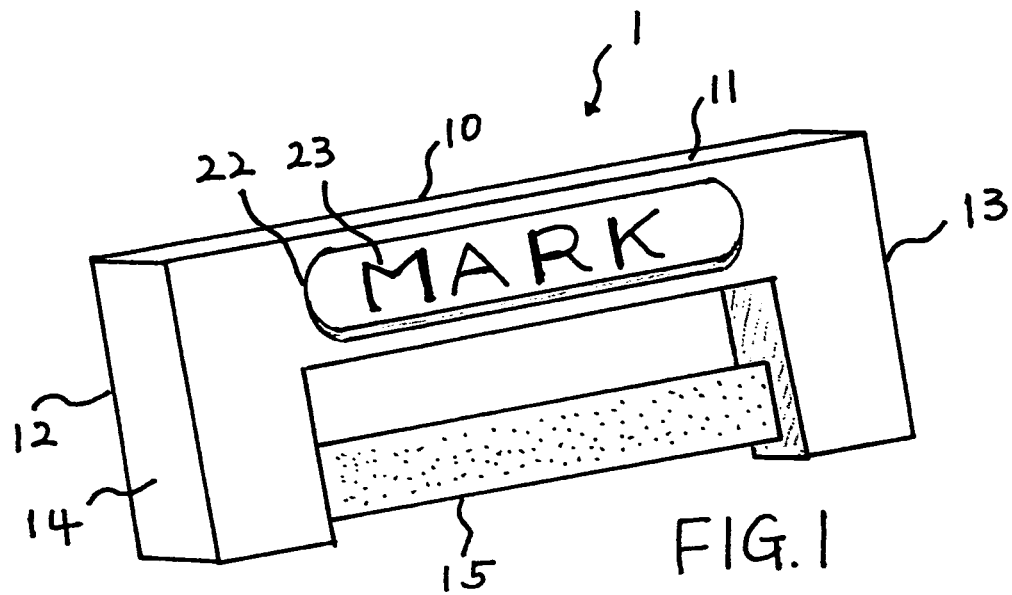
FIG. 1 is a perspective view of a preferred embodiment constructed according to the present invention.
Figure 2:
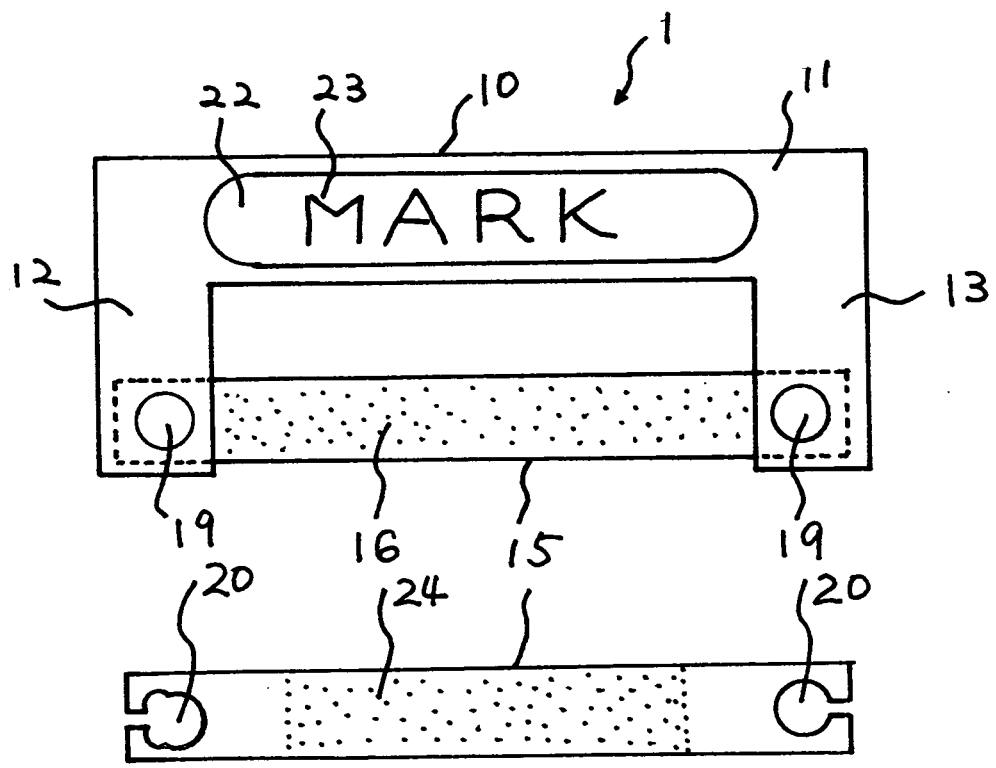
FIG. 2 is a horizontal front view of preferred embodiment shown in FIG. 1 of the present invention.
Figure 3:
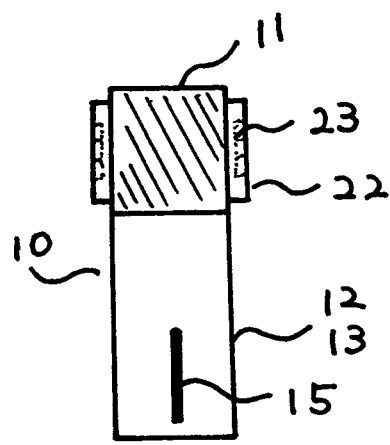
FIG. 3 is a vertical cross section view of the preferred embodiment according to the present invention.

The dental filing tool 1 shown as preferred embodiment in FIGS. 1 and 2, comprises of handle component 10 made of a formable material, not limited to but like plastic, which has a horizontal arm element 11 with a first vertical arm 12 extending downward from its first end and a second vertical arm 13 extending from its second end forming an arched structure. Between the first 12 and second vertical arms 13 is a filing strip 15 secured at each of its ends tautly with tension.

The one or both lateral sides of the filing strip 15 are coated with some superfine abrasive material 16, especially but not limited to diamond dust. The filing strip 15 is coated with abrasive material on its entire or partial surface 16 and 24. The filing strip 15 utilized in the dental filing tool 1 is of the appropriate thickness to be inserted into the interproximal area between teeth and/or crowns, bridges, onlays, or inlays, generally referred to as restorations.

The outside edges of the vertical arms 12, 13 have identical flat surface areas 14 on which opposable fingers may be placed to adeptly hold the dental filing tool 1 to facilitate an easy sawing back and forth movement to file, eliminating the cumbersome need to grip with both hands.

In the construction of the dental filing tool 1 according to fig. 2, the filing strip 15 has hole-like openings 19 at each of its ends to which each opening is fastened securely between the ends of the first 12 and second 13 vertical arms of the handle component 10 with sufficient tension creating a rigid filing and grinding surface.

In the construction of the dental filing tool 1 according to FIG. 2, the filing strip 15 has hole-like openings with slots 20.

Additionally in fig. 1, 2, 3 and 4 the horizontal arm element 11 of the handle 10 has on each side of the surface of the horizontal arm element a slightly raised flat segment made of but not limited to plastic 22 located on the center area. This facilitates maximum strength of the horizontal arm without adding bulk or compromising reach or access, and allows for the engravings of a mark, logo or letters 23.

Figure 4:
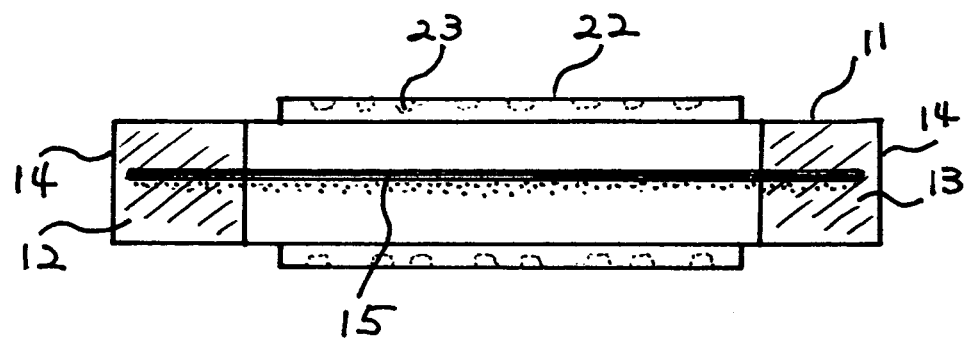
FIG. 4 is a plan view of preferred embodiment from the under side of the present invention.

Using the same means to facilitate maximum rigidity of the horizontal arm with maximum reach and access, fig. 4 depicts the raised flat segment 22.

Figure 5:
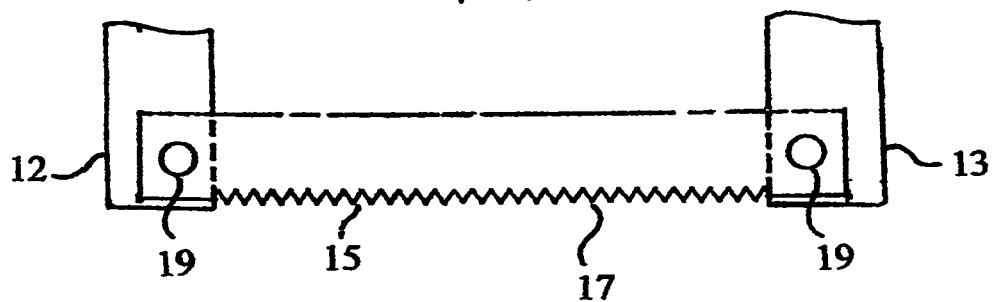
FIG. 5 is an alternate embodiment of the filing strip with a sawtooth cutting edge of the present invention.
Figure 6:
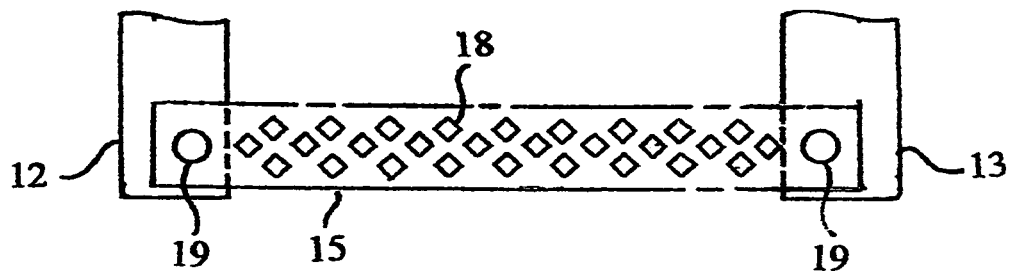
FIG. 6 is an alternate embodiment of the filing strip with multiple sharp edged perforations along the lateral surface of the present invention.

Depicted in figs. 5 and 6 are alternative embodiments of the dental filing tool 10 having a filing strip 15. In fig. 5 the alternate embodiment of the filing strip 15 has a cutting edge 17, including but not limited to sawteeth or serrated system provided along the longitudinal edge. In fig. 6, the alternate embodiment of the filing strip has multiple sharp edged perforations 18 along the lateral surface of the filing strip 15.

Figure 7:
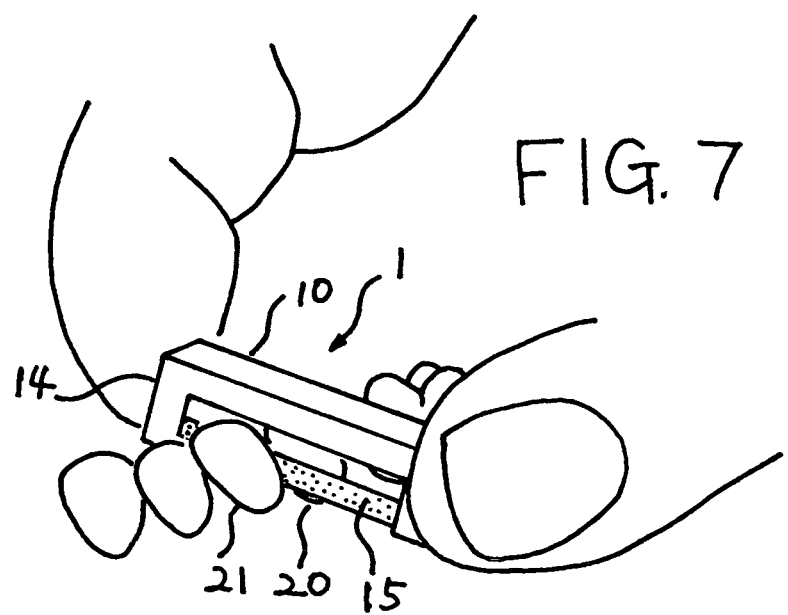
FIG. 7 is an elevational view depicting the insertion of the filing tool interproximally.

The dental filing tool 1 is used in the following manner as depicted in fig. 7. Initially the user holds the handle 10 placing opposable fingers on each flat surface area 14 of the vertical arms 12, 13 and aligns the filing strip 15 portion above the interproximal space between the tooth 20 and the restoration 21. The handle 10 is used to firmly insert the filing strip 15 into the interproximal space until stopped by proximal surface contact between tooth 20 and restoration 21. At which moment the user may, with applied pressure, commence a back and forth sawing motion with the slight movement of the opposable fingers or wrist to file down the proximal surface to create the appropriate interproximal distance.

It should be noted that while the handle component 10 maintains sufficient tension in the filing strip 15 to create a rigid surface, the slight malleability of the strip 15 still allows the user to manipulate the it with directional pressure applied through the handle 10 to form to any concavities along interproximal surfaces of anatomical contour of teeth. As the filing tool 1 is pulled back and forth between the area of proximal surface contact the abrasive lateral surface of the filing strip 15 gently removes enamel or restoration material in whatever conservative or aggressive increments desired by the user in relation to the repetitive filing motions and applied pressure.

It should also be appreciated that the beveling of the horizontal arm element 11 and vertical arm elements 12, 13 of the dental filing tool 1 is angled to such a degree to allow optimal access to the interproximal area between teeth and/or restorations. But while still maintaining adequate thickness to help prevent against the filing strip 15 slipping too deep inflicting undesirable cuts, nicks, and other injuries against gums.

Moreover, it should also be appreciated that the handle component 10 contains the filing strip 15 within a protective frame shielding the patient from suffering ambient cuts and nicks of the gums, lips, and cheek walls while the user is repositioning, re-angling, or moving the dental filing tool 1 within the mouth.

It will be understood that each of the elements described above, or two or more together may also find useful application in other types of methods differing from the types described above.

While the present invention has been described with reference to specific embodiments, it should be understood that it is not intended to be limited to the details described above. Those skilled in the art understand that various alterations, modifications, substitutions, or omissions of the forms and details of the preferred embodiment may be made without departing from the spirit and scope of this prevent invention. Therefore, it should be clearly understood that the descriptions and illustrations of the preferred embodiment are only to facilitate a clearer understanding of the invention and not used to unduly limit the scope of the present invention.

I claim:

1. A disposable dental filing tool, comprising:
   an arch shaped handle having a horizontal arm with first and second ends a first vertical arm attached at said first end and a second vertical arm attached at said second end; and
   a taut filing strip formed in said handle between said first vertical arm and said second vertical armed,
   wherein said filing strip has a sharp cutting edge system.

2. The disposable dental filing tool of claim 1, wherein said hole-like openings include slots cut into said first and second strip ends.

3. A disposable dental filing tool, comprising:
   an arch shaped handle having a horizontal arm with first and second ends, a first vertical arm attached at said first end and a second vertical arm attached at said second end; and
   a taut filing formed in said handle between said first vertical arm and said second vertical armed,
   wherein said filing strip has sharp-edged perforations along the lateral surface.

4. A disposable dental filing tool, comprising:
an arch shaped handle having a horizontal aim with first and second ends, a first vertical arm attached at said first end and a second vertical arm attached at said second end; and
a taut filing strip formed in said handle between said first vertical arm and said second vertical armed,
wherein said filing strip has first and second ends with hole-like openings.

5. A disposable dental filing tool, comprising:
an arch shaped handle having a horizontal arm with first and second ends, a first vertical arm attached at said first end and a second vertical arm attached at said second end; and
a taut filing strip formed in said handle between said first vertical arm and said second vertical armed,
wherein said handle component is made from a mold by injecting melted formable material into the mold and wherein said filing strip is inserted into the melted formable material.

6. A disposable dental filing tool, comprising:
an arch shaped handle having a horizontal arm with first and second ends, a first vertical arm attached at said first end and a second vertical arm attached at said second end; and
a taut filing strip formed in said handle between said first vertical arm and said second vertical armed,
wherein the horizontal arm is provided with a raised flat middle portion.

\* \* \* \* \*